(12) United States Patent
Sandvang et al.

(10) Patent No.: US 11,856,970 B2
(45) Date of Patent: Jan. 2, 2024

(54) BACILLUS SUBTILIS FOR ANIMAL FEED

(71) Applicant: CHR. HANSEN A/S, Hoersholm (DK)

(72) Inventors: Dorthe Sandvang, Hoersholm (DK); Ole Knudsmark Sjoeholm, Hoersholm (DK); Line Skjoet-Rasmussen, Hoersholm (DK); Jette Mundus Nielsen, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 862 days.

(21) Appl. No.: 16/471,298

(22) PCT Filed: Jan. 18, 2019

(86) PCT No.: PCT/EP2019/051262
§ 371 (c)(1),
(2) Date: Jun. 19, 2019

(87) PCT Pub. No.: WO2019/141815
PCT Pub. Date: Jul. 25, 2019

(65) Prior Publication Data
US 2021/0329944 A1  Oct. 28, 2021

(30) Foreign Application Priority Data
Jan. 19, 2018  (EP) .................... 18152596

(51) Int. Cl.
| | | |
|---|---|---|
| *A23K 50/40* | (2016.01) | |
| *A01N 63/22* | (2020.01) | |
| *A23K 10/18* | (2016.01) | |
| *C12N 1/20* | (2006.01) | |
| *C12R 1/125* | (2006.01) | |

(52) U.S. Cl.
CPC .............. *A23K 50/40* (2016.05); *A01N 63/22* (2020.01); *A23K 10/18* (2016.05); *C12N 1/205* (2021.05); *C12R 2001/125* (2021.05)

(58) Field of Classification Search
None
See application file for complete search history.

(56) References Cited

U.S. PATENT DOCUMENTS

| | | |
|---|---|---|
| 5,968,569 A | 10/1999 | Cavadini et al. |
| 10,006,073 B2 | 6/2018 | Nielsen et al. |
| 2013/0171204 A1 | 7/2013 | Dubourdieu et al. |
| 2017/0340683 A1 * | 11/2017 | Petri ........................ C12N 1/20 |
| 2017/0368118 A1 | 12/2017 | Grant et al. |

FOREIGN PATENT DOCUMENTS

| | | | |
|---|---|---|---|
| EP | 3 261 653 B1 | 1/2018 | |
| WO | WO-2016118840 A1 * | 7/2016 | ............. A23K 10/18 |

OTHER PUBLICATIONS

Ramachandran R., et al., "A Broad-Spectrum Antimicrobial Activity of Bacillus subtilis RLID 12.1", The Scientific World Journal, vol. 2014, pp. 1-10. (Year: 2014).*
"Guidance on the assessment of bacterial susceptibility to antimicrobials of human and veterinary importance," EFSA Journal (2012) 10(6):2740 pp. 1-10.
Felix et al., "Digestibility and fecal characteristics of dogs fed with Bacillus subtilis in diet," Ciencia Rural, Santa Maria, 40(10): 2169-2173 (2010).
Herstad et al., "Effects of a probiotic intervention in acute canine gastroenteritis—a controlled clinical trial," Journal of Small Animal Practice, 51: 34-38 (Jan. 2010).
Rivardo et al., "Anti-adhesion activity of two biosurfactants produced by *Bacillus* spp. prevents biofilm formation of human bacterial pathogens," Appl Microbiol Biotechnol 83:541-553 (Apr. 2009).
Rychen et al., "Safety and efficacy of Calsporin (Bacillus subtilis DSM 15544) as a feed additive for dogs," EFSA Journal 15(4):4760 pp. 1-9 (2017).
Schmitz et al., "Understanding the canine intestinal microbiota and its modification by pro-, pre-, and synbiotics—what is the evidence?" Veterinary Medicine and Science, 2: 71-94 (2016).
Wladyka et al., "A peptide factor secreted by *Staphylococcus pseudintermedius* exhibits properties of both bacteriocins and virulence factors," Scientific Reports, 5:14569, pp. 1-15 (Sep. 2015).

* cited by examiner

*Primary Examiner* — Michelle F. Paguio Frising
*Assistant Examiner* — Grant C Currens
(74) *Attorney, Agent, or Firm* — Foley & Lardner LLP (57) ABSTRACT

Described are the *Bacillus subtilis* strain deposited as DSM 32685 and mutant strains thereof which are susceptible to relevant antibiotics, have inhibitory activity against, for example, *Staphylococcus, Streptococcus, E. coli* and *Salmonella*, and have the ability to facilitate degradation of non-starch polysaccharides and thereby increase the amount of available oligosaccharides (sugar) in animal feed. Also described are compositions comprising at least one *Bacillus subtilis* strain of the disclosure and optionally further bacteria and/or one or more types of yeast and methods of using such compositions.

12 Claims, 1 Drawing Sheet

BACILLUS SUBTILIS FOR ANIMAL FEED

CROSS-REFERENCE TO RELATED APPLICATIONS

The present application is the U.S. National Stage of International Application No. PCT/EP2019/051262, filed Jan. 18, 2019, and claims priority to European Patent Application No. 18152596.5 filed Jan. 19, 2018.

FIELD OF THE INVENTION

The present invention relates to the *Bacillus subtilis* strain deposited as DSM 32685 and mutant strains thereof which are susceptible to relevant antibiotics, inhibit growth of multiple *Staphylococcus* spp., *Streptococcus canis*, *E. coli*, and *Salmonella enterica*, and which also have the ability to facilitate degradation of non-starch polysaccharides (NSP's) and thereby increase the amount of available oligosaccharides (sugar) in animal feed comprising non-starch polysaccharides thus providing a possibility for reducing the energy content of the feed without compromising the nutritional value of the feed.

A *Bacillus subtilis* strain of the invention may be formulated with animal feed ingredients as discussed in detail herein. Such compositions may be in the form of pellets that are extruded through standard pelleting processes.

The invention also provides a method for producing an animal feed, animal feed additive or premix comprising adding at least one *Bacillus subtilis* strain of the invention to an animal feed or relevant components thereof.

BACKGROUND OF THE INVENTION

*Bacillus* based probiotic feed additives are known for their positive effects on health in animal feed. These products are relevant for the feed industry because spores are heat stable and can survive the pelletizing process at temperatures up to 90-95° C. The endospore-forming bacteria *Bacillus subtilis* are Generally Regarded as Safe (GRAS) by the U.S. Food and Drug Administration (FDA) and acceptable for inclusion in an animal diet or water by the Association of American Feed Control Officials (AAFCO).

U.S. Pat. No. 5,968,569 (Nestec S. A.) discloses dried, ready-to-eat pet food kibbles which are coated with a probiotic microorganism, such as a *Bacillus subtilis*. The patent describes that a decrease of fecal pH and odors and a decrease of *Clostridium perfringens* abundance can be obtained by use of a product containing *Bacillus coagulans* but no results are provided with regard to the product of example 2 comprising a *Bacillus subtilis* and a *Bacillus licheniformis* strain.

Felix et al., Ciência Rural, Santa Maria, v. 40, n. 10, p. 2169-2173, out, 2010, describes a study wherein the diet digestibility and fecal characteristics of dogs fed with diets supplemented with *Bacillus subtilis* C-3102 (the *Bacillus subtilis* strain present in Calsporin®) was studied and it was found that dogs supplemented with the tested probiotic presented dryer feces, higher fecal score and reduced ammonia content compared to the control diet.

A review article by Schmitz and Suchodolski, Veterinary Medicine and Science, 2016, refers to the study by Felix et al., 2010, but finds that the clinical relevance of these findings is highly questionable. The review article also describes a study of acute gastroenteritis made by Herstad et al., 2010, Journal of Small Animal Practice (2010) 51, 34-38, wherein a probiotic mixture of *L. acidophilus, Pediococcus acidilactici, B. subtilis, B. licheniformis* and *L. farciminis* was used and it was found that the recovery time was significantly reduced. The review article does not indicate any additional studies performed with *Bacillus* species.

The safety and efficacy of Calsporin® (*Bacillus subtilis* C-3102, DSM 15544) as feed additive for dogs has been summarized in EFSA Journal 2017; 15(4):4760. Four studies were supplied aiming at investigating the effects of the supplementation of Calsporin® to the faecal consistency of dogs. Overall, there is a small but significant increase in faecal dry matter content and benefits seen in a subjective assessment of faecal consistency. However, the biological relevance of changes of this magnitude for the animal is considered questionable, as are the practical benefits for the owner.

US 2013/171204 (DuBourdieu et al) teaches that *Bacillus subtilis* can be incorporated into a feed for dog and was able to survive passage through the Gi tract and might be useful as a probiotic, but no specific strains are disclosed.

F. Rivardo, R. J. Turner, G. Allegrone, H. Ceri & M. G. Martinotti: "Anti-adhesion activity of two biosurfactants produced by *Bacillus* spp. prevents biofilm formation of human bacterial pathogens", Applied Microbiology and Biotechnology, vol. 83, no. 3, 2009, pages 541-553, describes production of biosurfactant and thereby ability to inhibit biofilm formation of two different *Bacillus* species (*Bacillus subtilis* and *Bacillus licheniformis*).

The abstract discloses that "The two biosurfactants showed interesting specific anti-adhesion activity being able to inhibit selectively biofilm formation of two pathogenic strains: *Escherichia coli* CFT073 and *Staphylococcus aureus*. ATCC 29213 biofilm formation was decreased of 97% and 90%, respectively. The V9T14 biosurfactant active on the Gram-negative strain was ineffective against the Gram-positive and the opposite for the V19T21. This activity was observed either by coating the polystyrene surface or by adding the biosurfactant to the inoculum."

However, the anti-adhesion activity is not an inhibitory effect as also stated in the article on page 548, second column, lines 4-6: "There was no apparent effect on planktonic survivability (FIG. 8) by the presence of V9T14 (p=0.46) and V19T21 (p=0.38) biosurfactants, at every concentration tested. V9T14 biosurfactant was not able to inhibit the adhesion of other microorganisms (FIG. 9a), in particular *S. aureus* ATCC 29213, *P. aeruginosa* PA14, and the isolate *S. epidermidis.*"

The present patent application provides no disclosure about any specific anti-adhesion activity against biofilm formation but demonstrates the inhibitory effects of the *Bacillus subtilis* strain DSM 32685 against several pathogen bacteria using two different methods: solid agar and inhibition in broth. As evident from the examples of present application DSM 32685 demonstrates inhibition of bacterial growth and not just inhibition of bacterial adhesion.

The inhibitory effect of the *Bacillus subtilis* strain DSM 32685 in the present application might be compared with "the planktonic survivability" (FIG. 8) where the mean viable CFU are depictured. And the differences are obvious: Rivardo et al. obtain no apparent effect on planktonic survivability whereas the present patent application reveals inhibition against multiple pathogenic bacteria and in different assays.

In conclusion: None of the two *Bacillus* species investigated in Rivardo et al. show decrease in biofilm formation against multiple pathogen strains, whereas DSM 32685 shows inhibitory effect on growth for all pathogens investigated.

SUMMARY OF THE INVENTION

Successful isolation of a microorganism with probiotic capability is most often seen when the bacterial species has been isolated from an animal environment. *Bacillus subtilis* is a ubiquitous Gram-positive, rod-formed, spore-forming microorganism which can be part of a dog's natural intestinal flora. The *Bacillus subtilis* strain deposited as DSM 32685 has been isolated from the feces of a healthy dog meaning that it is likely to be adapted to the canine environment.

The *Bacillus subtilis* strain deposited as DSM 32685 has been found to inhibit the growth of the opportunistic pathogen *Staphylococcus* pseudintermedius, and also to reduce the growth rate of the Group G *Streptococcus canis*. DSM 32685 has further been found to inhibit the growth of the Gram-negative pathogens *E. coli* and *Salmonella enterica*. Furthermore, *Bacillus subtilis* DSM 32685 is more effective at facilitating degradation of non-starch polysaccharides from dog feed than two commercial strains marketed for animal feed use, DSM 19489 and a *Bacillus subtilis* strain isolated from Calsporin®. To the best of the knowledge of the present inventors, the finding that a *Bacillus* strain can facilitate the release of a high amount of sugar compounds from a pet feed such as a dog feed has not been disclosed in the prior art.

The inhibition of *Staphylococcus* pseudintermedius known to cause skin infections in dogs was tested using an agar well diffusion method as described in detail in the examples. As evident from the results, the inhibition of *Staphylococcus* pseudintermedius was seen in four different strains of *Staphylococcus* pseudintermedius and only for *Bacillus subtilis* DSM 32685 and not for the three other *Bacillus subtilis* tested, DSM 32686, DSM 19489, and the *Bacillus subtilis* strain isolated from Calsporin®. To the best of the knowledge of the present inventors, this property has not been reported previously for a *Bacillus subtilis* strain.

The opportunistic pathogen *Streptococcus canis* found in upper respiratory tract in carnivores is known to cause skin infections and to be associated with endometritis and pyometra, a uterine bacterial infection which is a frequent disease affecting intact female dogs and which can be life threatening in dogs. Potential for inhibition of *Streptococcus canis* was done in a "time kill assay" design measuring pathogen growth inhibition in a broth as described in detail in the examples. During a 24 hour growth period, the *Streptococcus canis* grew from $10^2$ CFU/ml to $10^8$ CFU/ml. This was also the case for samples containing both *Streptococcus canis* and growth supernatant of the three other strains tested including DSM 19489 and the *Bacillus subtilis* strain isolated from Calsporin®. When *Streptococcus canis* was grown together with *Bacillus subtilis* DSM 32685 supernatant it grew from $10^2$ CFU/ml to $10^5$ CFU/ml i.e. a 1000 fold reduction of the pathogen compared to the control.

To the best of the knowledge of the present inventors, this property has not been reported previously for a *Bacillus subtilis* strain and is not found by the three other strains tested, DSM 32586, DSM 19489 and the *Bacillus subtilis* strain isolated from Calsporin®.

Degradation of non-starch polysaccharides from dog feed was tested as described in Example 2. It was found that *Bacillus subtilis* DSM 32685 could release 685±27 Kj/Kg, *Bacillus subtilis* DSM 19489 could release 438±37 Kj/Kg and the *Bacillus subtilis* strain isolated from Calsporin® could release 117±9 Kj/Kg in standard dog feed as an average of 2 repeated analyses. The facilitation of the release of a high amount of sugar compounds from dog feed provides a possibility for reducing the energy content of the feed without comprising the nutritional value of the feed.

The inhibition of the Gram-negative pathogens *E. coli* and *Salmonella enterica* was tested using an agar well diffusion method as described in detail in Example 3. As evident from the results, the inhibition of *E. coli* was seen in two different strains and only for *Bacillus subtilis* DSM 32685 and not for the three other *Bacillus subtilis* tested, DSM 32686, DSM 19489, and the *Bacillus subtilis* strain isolated from Calsporin®. Similarly, the inhibition of *Salmonella enterica* was seen in five different strains and only for *Bacillus subtilis* DSM 32685 and not for the three other *Bacillus subtilis* tested, DSM 32686, DSM 19489, and the *Bacillus subtilis* strain isolated from Calsporin®.

To the best of the knowledge of the present inventors, this property has not been reported previously for a *Bacillus subtilis* strain.

In conclusion, these studies have demonstrated that the *Bacillus subtilis* strain deposited as DSM 32685 is susceptible to ampicillin, vancomycin, gentamicin, kanamycin, streptomycin, erythromycin, clindamycin, tetracycline, and chloramphenicol tested after the CLSI guidelines (M07-A8 and M45-A2); exhibits an inhibition zone of at least 1 mm for *Staphylococcus* pseudintermedius; and reduces the growth rate of *Streptococcus canis* by at least one Log10 growth in 24 hours; and has the ability to facilitate degradation of non-starch polysaccharides and thereby increase the amount of available oligosaccharides in animal feed with at least 500 kJ/kg feed when tested in the DNS assay of example 2.

The present invention provides a *Bacillus subtilis* strain selected from the group consisting of the strain deposited as DSM 32685 and a mutant strain of DSM 32685 having these properties.

It has been found that DSM 32685 exhibits an inhibition zone of at least 1 mm for the Gram-negative pathogens *E. coli* and *Salmonella enterica*. Preferred mutants of the strain also exhibit this property.

A bacterial strain refers to a bacterium which remains genetically unchanged when grown or multiplied. The multiplicity of such identical bacteria is included when reference is made to a strain.

Compositions comprising at least one *Bacillus subtilis* strain according to the invention, e.g. as a probiotic, a Direct Fed Microbial (DFM), an animal feed additive or premix, or an animal feed, such as complete feed, may be fed to an animal.

The at least one *Bacillus subtilis* strain according to the invention may be added to the feed during production, after production by the supplier or by the person feeding the animal, just prior to providing the feed to the animal. The *Bacillus subtilis* bacteria used in the methods and compositions described herein are particularly suitable because they are capable of surviving (as spores) the heat and pressure conditions of the process of producing a dry pelleted feed product.

Definitions

In general, the terms and phrases used herein have their art-recognized meaning, which can be found by reference to standard texts, journal references, and context known to those skilled in the art. The following definitions are provided to clarify their specific use in context of the disclosure.

As used herein, the singular forms "a", "an" and "the" are intended to include the plural forms as well, unless the context clearly indicates otherwise.

Animal: The term "animal" includes, but is not limited to canine (e.g., dogs), feline (e.g., cats); equine (e.g., horses), bovine (e.g., cattle), ovine (e.g. sheep), caprine (e.g. goat) porcine animals (e.g. swine, such as piglets, weaners, growers, finishers, hocks, polts, gilts, sows, gestation sows) and rabbit, as well as avians including, but not limited to, poultry such as broilers, breeders, layers, ostriches, quails, turkeys, ducks, geese, domestic fur animals such as ferrets, minks, mustelids, ruminants such as cattle, sheep, goats, camels, and giraffes, and fish such as fin-fish, shellfish, and other aquatic animals. Fin-fish include all vertebrate fish, which may be bony or cartilaginous fish, such as salmon, trout, tilapia, catfish and carps and shellfish include, but are not limited to clams, lobster, shrimp, crab, prawns and oysters.

Animal feed: The term "animal feed" refers to any compound, preparation, or mixture suitable for, or intended for intake by an animal. Animal feed may comprise concentrates as well as for example vitamins, minerals, enzymes, amino acids and/or other feed ingredients (such as in a premix). The animal feed may further comprise forage.

Complete feed: The term "complete feed" is often used for animal feed for pets such as dogs and cats and refers to a ready-to-eat animal feed which comprises concentrates as well as for example vitamins, minerals, enzymes, amino acids and/or other feed ingredients (such as in a premix). An example of a complete feed for a dog is given in Example 1.

Composition: The term "composition" refers to a composition comprising a carrier and at least one bacterial strain as described herein. The composition will further comprise minor amounts of components resulting from the fermentation process, such as an oil used as a surfactant. The compositions described herein may be a probiotic, a Direct Fed Microbial (DFM), an animal feed additive or premix, or an animal feed such as complete feed.

Concentrate: The term "concentrate" means a feed with high protein and energy concentrations, such as fish meal, molasses, oligosaccharides, sorghum, seeds and grains (either whole or prepared by crushing, milling, etc. from, e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Direct Fed Microbial: The term "direct fed microbial" or "DFM" means live micro-organisms including spores which, when administered in adequate amounts, confer a benefit, such as improved digestion or health, on the host.

Effective amount/concentration/dosage: The terms "effective amount", "effective concentration", or "effective dosage" are defined as the amount, concentration, or dosage of the bacterial strain(s) sufficient to improve the wellness, health, digestion or yield of an animal. The actual effective dosage in absolute numbers depends on factors including the state of health of the animal in question. The "effective amount", "effective concentration", or "effective dosage" of the bacterial strains may be determined by routine assays known to those skilled in the art.

Feeding an animal: The terms "feeding an animal" or "fed to an animal" means that the composition of the present invention is administered orally to the animal in an effective amount. The oral administration may be repeated, e.g. one or more times daily over a specified time period such as several days, one week, several weeks, one months or several months. Accordingly, the terms "feeding" or "fed" mean any type of oral administration such as administration via an animal feed or via drinking water or, in certain circumstances, by oral gavage or aerosol spray.

Inhibitory activity against *Staphylococcus* pseudintermedius: The term "inhibitory activity against *Staphylococcus* pseudintermedius" means that the growth of *Staphylococcus* pseudintermedius is inhibited and/or that some or all of the *Staphylococcus pseudintermedius* are killed. The inhibition can be determined by the assay described in Example 1.

Inhibitory activity against *Streptococcus canis*: The term "inhibitory activity against *Streptococcus canis*" means that the growth of *Streptococcus canis* is inhibited and/or that some or all of the *Streptococcus canis* are killed. This can be determined by the assay described in Example 1.

Inhibitory activity against *E. coli*: The term "inhibitory activity against *E. coli*" means that the growth of *E. coli* is inhibited. This can be determined by the assay described in Example 3.

Inhibitory activity against *Salmonella enterica*: The term "inhibitory activity against *Salmonella enterica*" means that the growth of *Salmonella enterica* is inhibited. This can be determined by the assay described in Example 3.

Isolated: The term "isolated" means that the bacterial strains described herein are in a form or environment which does not occur in nature, i.e. the strain is at least partially removed from one or more or all of the naturally occurring constituents with which it is associated in nature.

Monogastric animal: Monogastric animals include, but are not limited to, poultry such as broilers, breeders, layers, turkey, ostriches, quails, ducks, and geese, herbivores, such as horses, swine, such as piglets, weaners, growers, finishers, hocks, polts, gilts, sows, gestation sows, rodents such as rabbits, pets such as cats and dogs and fish (including but not limited to salmon, trout, tilapia, catfish and carps) and crustaceans (including but not limited to shrimps and prawns). Pigs, poultry, ferret, and mink as well as companion animals such as dogs and cats are preferred monogastric animals.

Non-starch polysaccharides (NSP): The term "non-starch polysaccharides" is defined as described in US2014/034933, now granted as U.S. Pat. No. 10,006,073, as the part of the crude carbohydrate fraction when sugar (mono- and oligosaccharides), organic acids and starch are taken away. Carbohydrates are classified according to the degree of polymerization (DP): mono- and disaccharides (DP=1-2), oligosaccharides (DP=3-9) and polysaccharides (DP≥10). Polysaccharides are further divided into two subgroups according to their digestibility: starch and non-starch polysaccharides. Consistent with the above, the term "non-starch polysaccharides (NSP)" in the present description and claims is defined as polysaccharides with a degree of polymerization≥0.10 excluding starch. Non-starch polysaccharides consist of many different plant polymers, including i.e. β-glucans, cellulose, hemicellulose, and pectic substances. Non-starch polysaccharides can be determined by gas-liquid chromatography (component neutral sugars) and by colorimetry (uronic acids).

Pellet: The terms "pellet" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

Pet: The term "pet" refers to companion animals such as domestic cat and domestic dog, ferrets, rats, rabbit, hamster, guinea pig, reptiles, birds such as parakite, parrot, falcon, hawk.

Pet food: The term "pet food" includes a dry, semi-moist or a moist (wet) product. Wet food includes food that has a moisture content of 70%-90% and is usually sold in containers such as tins, pouches and/or trays. Dry food includes food having a similar composition but with 5%-15% moisture, often presented as small biscuit-like kibbles. Semi-moist food includes food having a moisture content of from above 15% up to 70%. The amount of moisture in any product may influence the type of probiotic bacteria that can be added. The food product, of any moisture level, may be ready to eat. Pet food snack includes snack bars, cereal bars, snacks, biscuits, drinks (e.g. cat milk) and sweet products.

The pet food product may be a cooked product, it may incorporate meat or animal derived material (such as beef, chicken, eggs, turkey, lamb, fish, blood marrow, marrow-bone, etc. or by-products hereof). Alternatively, the composition may be meat-free (preferably including a meat substitute such as soya, maize, gluten or a soya product) in order to provide protein. The composition may contain additional protein sources such as soya protein concentrate, milk, protein, gluten etc. The composition may also include starch, such as one or more grains (e.g. wheat, corn, rice, oats, barley etc.) or may be starch free. The composition may incorporate or may be a gelatinized starch matrix. The composition may incorporate one or more types of fibre such as sugar beet pulp, chicory pulp, chicory, coconut endosperm fibre, wheat fibre, fructooligosaccharides, galactooligosaccharides, inulin etc. The fibre may be a prebiotic. The combination of the probiotic and the prebiotic may form a synbiotic combination. Dairy products such as those incorporating a cream or a cheese may be suitable. The most suitable composition is pet food described herein which is sold as a pet food and in particular a pet food for a domestic dog or a domestic cat. Preferably, the pet food is in a dry format, such as a dried ready-to-eat cereal product comprising a cooked starch matrix produced by extrusion cooking and referred to as pet kibble.

Premix: The term "premix" refers to a composition comprising at least one strain added to a carrier to make a premix which is then added to an animal feed at a desired inclusion rate.

Prevention, reduction or control of a bacterial colonization or infection: As used herein the terms "preventing", "reduction" or "control" of a bacterial colonization or infection refer to any and all applications that prevent, reduce or control a bacterial colonization or infection including a reduction or lowering of the number of bacteria or hindering of the outgrowth of bacteria.

Probiotic: Probiotics—in some parts of the world called Direct Fed Microbials (DFM's)—are often described as dietary supplements containing potentially beneficial bacteria and according to the currently adopted definition are live micro-organisms which can confer a health benefit on the host. Probiotic micro-organisms assist the body's naturally occurring gut flora to re-establish themselves. Probiotic micro-organisms are reported and known to strengthen the immune system and prevent infections, reduce inflammation, improve mineral absorption and prevent the growth of harmful bacteria.

Protein: The term "protein" refers to any compound, preparation or mixture that includes at least one protein derived from or originating from a vegetable or animal source, including modified proteins and protein-derivatives. Vegetable proteins may be derived from vegetable protein sources, such as legumes and cereals, for example materials from plants of the families Fabaceae (Leguminosae), e.g. soybean, lupine, pea, or bean; Cruciferaceae, Chenopodiaceae, e.g. beet, sugar beet, spinach or *quinoa*; and Poaceae. Other examples of vegetable protein sources are cereals such as barley, wheat, rye, oat, maize (corn), rice, and sorghum. Animal proteins are derived from animal protein sources such as meat sources e.g. poultry, lamb, pork, fish or animal by-products e.g. fish and bone meal.

Reducing sugar: A reducing sugar is any sugar that either has a reactive aldehyde group or is capable of forming one to allow the sugar to act as a reducing agent. The reducing ends are formed by the enzymatic cleavage of the glycosidic bond between polymeric carbohydrates. Reducing sugars include glucose, glyceraldehyde and galactose as well as disaccharides, like lactose and maltose and can be measured by the Nelson-Somogyi (NS) or dintrosalicylic acid (DNS) method. DNS is an aromatic compound that reacts with reducing sugars and other reducing molecules to form 3-amino-5-nitrosalicylic acid, which absorbs light strongly at 540 nm. The assay simulates the situation when feed is ingested by the animal and is digested in the digestive tract. The ability of different *Bacillus subtilis* strains to degrade non-starch polysaccharides (NSP's) to reducing sugars has been investigated in Example 2.

Susceptibility to antibiotics: The term "susceptible to antibiotics" means the phenotypic property of a bacterial strain, that growth of said bacterial strain is inhibited under conditions where the bacterial strain would otherwise grow. In this context susceptibility to antibiotics is tested after the CLSI guidelines (M07-A8 and M45-A2). A strain of *Bacillus* is considered susceptible if growth is only detected at or below the breakpoint concentration specified in EFSA Journal 2012; 10(6):2740 for vancomycin, gentamicin, kanamycin, streptomycin, erythromycin, clindamycin, tetracycline, and chloramphenicol. With regard to ampicillin there is no breakpoint given by EFSA for *Bacillus*; the breakpoint 4 mg/L has been chosen for a strain to be considered susceptible.

Spore: The terms "spore" and "endospore" are interchangeable and have their normal meaning which is well known and understood by those of skill in the art. As used herein, the term spore refers to a microorganism in its dormant, protected non-reproductive state.

Stable: The term "stable" is a term that is known in the art, and in a preferred aspect, stable is intended to mean the ability of the microorganism to remain in a live form until it is administered to an animal to improve the health of the animal.

DETAILED DISCLOSURE OF THE INVENTION

The present invention provides a *Bacillus subtilis* strain selected from the group consisting of the strain deposited as DSM 32685 and a mutant strain of DSM 32685 which is susceptible to ampicillin, vancomycin, gentamicin, kanamycin, streptomycin, erythromycin, clindamycin, tetracycline, and chloramphenicol tested after the CLSI guidelines (M07-A8 and M45-A2); exhibits an inhibition zone of at least 1 mm for *Staphylococcus* pseudintermedius, *E. coli*, and *Salmonella enterica*, and reduces the growth rate of *Streptococcus canis* by at least one Log10 growth in 24 hours, and which optionally also has the ability to facilitate degradation of non-starch polysaccharides and thereby increase the amount of available oligosaccharides in animal feed with at least 500 kJ/kg feed when tested in a DNS assay as described in Example 2.

The bacterial strains described herein are isolated, i.e. present in a form or environment which does not occur in nature.

A "mutant bacterium" or a "mutant strain" refers to a natural (spontaneous, naturally occurring) mutant bacterium or an induced mutant bacterium comprising one or more mutations in its genome (DNA) which are absent in the parent strain DNA. An "induced mutant" is a bacterium where the mutation was induced by human treatment, such as treatment with any conventionally used mutagenization treatment including treatment with chemical mutagens, such as a chemical mutagen selected from (i) a mutagen that associates with or become incorporated into DNA such as a base analogue, e.g. 2-aminopurine or an interchelating agent such as ICR-191, (ii) a mutagen that reacts with the DNA including alkylating agents such as nitrosoguanidine or hydroxylamine, or ethane methyl sulphonate (EMS) or N-methyl-N'-nitro-N-nitroguanidine (NTG), UV- or gamma radiation etc. In contrast, a "spontaneous mutant" or "naturally occurring mutant" has not been mutagenized by man.

A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1%, less than 0.01%, less than 0.001% or even less than 0.0001% of the nucleotides in the bacterial genome have been replaced with another nucleotide, or deleted, compared to the mother strain.

Mutant bacteria as described above are non-GMO, i.e. not modified by recombinant DNA technology. As an alternative to the above preferred method of providing the mutant by random mutagenesis, it is also possible to provide such a mutant by site-directed mutagenesis, e.g. by using appropriately designed cloning techniques.

When the mutant is provided as a spontaneously occurring mutant the strain is subjected to the selection step without any preceding mutagenization treatment.

In one embodiment, the *Bacillus subtilis* strain of the invention has at least 98% (such as at least 98.5%, such as at least 99%, such as at least 99.5%, such as at least 99.6%, such as at least 99.7%, such as at least 99.8%, such as at least 99.9%) sequence identity to the nucleotide sequence of DSM 32685.

In one embodiment, the *Bacillus subtilis* strain of the invention has at least 98% (such as at least 98.5%, such as at least 99%, such as at least 99.5%, such as at least 99.6%, such as at least 99.7%, such as at least 99.8%, such as at least 99.9%) sequence identity to the amino acid sequence of DSM 32685.

A strain is considered to exhibit an inhibitory activity towards *Staphylococcus* pseudintermedius if the inhibition zone is at least 1 mm (low inhibition). Preferably, the inhibition zone is at between at least 1 mm and 2 mm (medium), more preferably more than 2 mm (high). The inhibition zone may be different for the various *Staphylococcus* pseudintermedius strains. For a strain to be considered to exhibit an inhibitory activity against *Staphylococcus* pseudintermedius according to the present invention it should exhibit an inhibition zone of at least 1 mm for all of the *Staphylococcus* pseudintermedius strains tested. Preferably, the inhibition zone of two, three, or even more preferably the inhibition zone of all four of the *Staphylococcus* pseudintermedius strains is at least between 1 mm and 2 mm. Even more preferably, the inhibition zone of two, three, or even more preferably the inhibition zone of all four of the *Staphylococcus* pseudintermedius strains is more than 2 mm.

Similarly, a strain is considered to exhibit an inhibitory activity towards *E. coli* and/or *Salmonella enterica* if the inhibition zone is at least 1 mm (low inhibition) for the species in question. Preferably, the inhibition zone is between at least 1 mm and 2 mm (medium), more preferably more than 2 mm (high). The inhibition zone may be different for the various *Staphylococcus* pseudintermedius, *E. coli*, and *Salmonella enterica* strains. For a strain to be considered to exhibit an inhibitory activity against *E. coli* and *Salmonella enterica* according to the present invention it should exhibit an inhibition zone of at least 1 mm for both of the *E. coli* and all of the five *Salmonella enterica* strains tested. Preferably, the inhibition zone of two, three, or even more preferably the inhibition zone of all both of the *E. coli* and all of the five *Salmonella enterica* strains is at least between 1 mm and 2 mm. Even more preferably, the inhibition zone for both of the *E. coli*, and the inhibition zone of two, three, four, or even more preferably the inhibition zone of all of the five *Salmonella enterica* strains is more than 2 mm.

A strain is considered to exhibit an inhibitory activity towards *Streptococcus canis* if the strain reduces the growth rate of *Streptococcus canis* by at least one Log10 growth in 24 hours. Preferably, the reduction of the Log10 growth in 24 hours is at least 2, more preferably at least 3.

Probiotics—in some parts of the world called Direct Fed Microbials or DFM's—are sometimes fed to help minimize negative digestive effects of ingesting feed or food that are relatively hard for the animal to digest. Results of ingesting feed or food with indigestible fibre that cannot be fully digested such as non-starch polysaccharides (NSP) may be flatulence. Flatulence may occur due to bacterial action upon undigested and unassimilated NSP's.

The *Bacillus subtilis* strains of the present invention have the ability to facilitate degradation of non-starch polysaccharides (NSP's) and thereby increase the amount of available oligosaccharides (sugar) in animal feed comprising NSP's. The ability of different *Bacillus* strains to degrade NSP to reducing sugars has been investigated in Example 2 and the results are provided in Table 3. Strains having the ability to increase the available sugar amount with at least 500 kJ/kg feed when tested as outlined in the example are considered preferable.

Based on the detailed assay descriptions the person of ordinary skill in the art is able to repeat these assays to determine whether a specific *Bacillus subtilis* strain complies with the antibiotic susceptibility, the inhibitory activity and the capability of degrading NSP. In this manner the person of ordinary skill in the art will be able to consistently produce strains with the stated properties.

The invention further provides a composition comprising at least one *Bacillus subtilis* strain of the invention. The compositions according to the invention may comprise a combination of at least one of the *Bacillus subtilis* strains of the invention and at least one other strain. The composition may comprise at least two strains, such as at least three, such as at least four, such as at least five strains, at least one of which is a *Bacillus subtilis* strain of the present invention.

In a particular embodiment, the composition further comprises a bacterium from one or more of the following strains of *Bacillus*: *Bacillus amyloliquefaciens*, *Bacillus subtilis*, *Bacillus pumilus*, *Bacillus polymyxa*, *Bacillus licheniformis*, *Bacillus megaterium*, *Bacillus coagulans*, *Bacillus circulans*, *Bacillus simplex*, *Bacillus mojavensis*, *Bacillus safensis*, *Bacillus simplex*, *Bacillus atrophaeus*, *Bacillus methylotrophicus*, *Bacillus siamensis*, *Bacillus vallismortis*, *Bacillus tequilensis* or any combination thereof.

In a further embodiment, the composition comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

Preferred examples of such bacteria are the species *Bifidobacterium* spp., *Bifidobacterium breve, Bifidobacterium animalis, Bifidobacterium lactis, Bifidobacterium longum, Bifidobacterium bifidum, Lactococcus lactis, Lactococcus cremoris, Lactobacillus acidophilus, Lactobacillus casei, Lactobacillus kefir, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sake, Lactobacillus reuteri, Lactobacillus lactis, Lactobacillus delbreuckii, Lactobacillus plantarum, Lactobacillus johnsonii* and *Streptococcus thermophilus*.

Particularly preferred strains are *Bifidobacterium animalis* subsp *lactis*, e.g. the strains deposited as DSM 15954 (marketed by Chr. Hansen A/S, Denmark, as BB-12®); ATCC 27536, and DSM 10140, respectively; *Lactobacillus acidophilus*, e.g. the strain deposited as DSM 13241, *Lactobacillus rhamnosus*, e.g. the strain deposited as ATCC 53103, *Lactobacillus paracasei* subsp. *paracasei*, e.g. the strains deposited as ATCC 55544 and CCTCC M204012, respectively, *Lactobacillus reuteri*, e.g. the strain deposited as ATCC 55845, *Lactobacillus rhamnosus*, e.g. the strain deposited as ATCC 55826, *Lactobacillus paracasei*, e.g. the strain deposited as LMG-P-17806, *Streptococcus thermophilus*, e.g. the strain deposited as DSM 15957, and *Lactobacillus fermentum*, e.g. the strain deposited as NM02/31074.

In a particular embodiment, the composition further comprises one or more types of yeast. The one or more types of yeast can be selected from the group consisting of Saccharomycetaceae, *Saccharomyces* (such as *S. cerevisiae* and/or *S. boulardii*), *Kluyveromyces* (such as *K. marxianus* and *K. lactis*), *Candida* (such as *C. utilis*, also called *Torula* yeast), *Pichia* (such as *P. pastoris*), *Torulaspora* (such as *T. delbrueckii*), *Phaffia* yeasts and Basidiomycota.

If more than one strain is used, it is contemplated that the proportion of each strain in the composition will be 1 to 99%, such as 20 to 80%, e.g. 30 to 70%, more particularly 20%, 33%, 40% or 50% of the total amount of bacterial isolates calculated as CFU/g composition. The individual strains may be present in about equal numbers or in unequal numbers.

The relevant strain or strains are provided in a commercially relevant form known to the skilled person. Accordingly, in an embodiment the strain or strains of the composition are present in a dried (e.g. spray dried) or frozen form. The composition may be provided in any suitable form such as in the form of a liquid e.g. a gel, a slurry, a powder or a pellet.

In a preferred embodiment, the composition comprises from $10^5$ to $10^{12}$ CFU/g, more preferably from $10^6$ to $10^{12}$ CFU/g, and most preferably from $10^7$ to $10^{12}$ CFU/g, such as from $10^8$ to $10^{11}$ CFU/g, e.g. from $10^9$ to $10^{10}$ CFU/g of each of the bacterial strains in the composition. The composition comprises at least $5 \times 10^4$ CFU of each strain per gram of the composition which distinguishes a composition of the present invention from e.g. animal feed with naturally occurring strains.

The term "CFU/g" relates to the gram weight of the composition including carriers such as calcium carbonate, anti-caking agents such as aluminium silicates and kieselgur (diatomaceous earth), and other components present in the composition.

Compositions of the present invention include at least one *Bacillus subtilis* strain of the invention and at least one carrier, excipient and/or diluent and/or other component that make the composition suitable for feeding to an animal or as an additive for drinking water. Where administered to an animal, it will be non-toxic to the animal. There are a myriad of such agents available which may be added. Without intending to be limiting, examples include standardizing agents, extenders, wetting agents and lubricating agents, preservative agents, lipids, stabilizers, solubilizers, free flowing agents, and emulsifiers. Examples that may be particularly useful in administration to an animal include ground corn cobs, salt, ground limestone, calcium carbonate, sodium bentonite, zeolites, ground soy hulls, citrus pulp, dairy by-products, animal protein products, grain products, plant protein products, processed grain products and by-products, roughage products, molasses products fermentation by-products such as dried distillers grains and/or solubles, citric acid and glutamic acid fermentation by-products and the like.

*Bacillus* bacteria exist as spores and vegetative cells which can divide to produce more vegetative cells. When reference is made herein to *Bacillus*, this relates to both spores and vegetative cells unless the context indicates otherwise.

In the composition of the present invention, the *Bacillus* strain or strains are preferably provided as spores. The primary function of sporulation is generally to ensure the survival of a bacterium through periods of environmental stress. They are therefore resistant to ultraviolet and gamma radiation, desiccation, lysozyme, temperature, starvation, and chemical disinfectants. The spore coat is impermeable to many toxic molecules and may also contain enzymes that are involved in germination. The core has normal cell structures, such as DNA and ribosomes, but the spore is metabolically inactive.

The vegetative form of the bacteria produces effectors which may reduce the numbers of bacterial pathogens or have other beneficial effects in the gastrointestinal tract of an animal. Thus, reactivation and germination of the spores after administration to the animal is important.

It is known from the literature that bile can have some negative influences on the survival and germination and outgrowth to vegetative cells in the GIT of animals. Therefore probiotic bacteria shall generally be able to survive and proliferate in the gut of animals by being able to tolerate a low pH and resistant to bile salt in order to be useful as probiotic compositions for the addition to animal feed. The ability to be able to form endospores makes *Bacillus* particularly suitable as probiotics.

In one aspect, the present invention provides an animal feed, animal feed additive or premix comprising at least one *Bacillus subtilis* strain according to the invention, and further comprising one or more of concentrate(s), vitamin(s), mineral(s), enzyme(s), amino acid(s) and/or other feed ingredient(s). In one embodiment, the animal feed, animal feed additive or premix comprises the *Bacillus subtilis* strain DSM 32685. In another embodiment, the animal feed, animal feed additive or premix comprises a mutant of the *Bacillus subtilis* strain DSM 32685.

In a specific embodiment, the animal feed comprises forage. Generally, the forage comprises a vegetable protein source. In a particular embodiment, the vegetable protein source is material from one or more plants of the family Fabaceae. In another particular embodiment, the vegetable protein source is material from one or more plants of the family Chenopodiaceae. Other examples of vegetable protein sources are rapeseed and beans.

Animal feed for carnivores and omnivores, e.g. pets such as cats and dogs, generally comprising a starch source, texturized proteins, or semi-moist pieces can be produced using typical ingredients used to manufacture pet food such as grain sources (e.g., corn, rice, wheat, bailey), protein sources (e.g., meat sources such as poultry, beef, lamb, pork, fish) or animal by-products e.g. fish and bone meal, vegetable sources (e.g., soy, corn gluten, casein, whey, eggs); fats (e.g., vegetable oils, animal fats, fish oils), plant fibres (beet pulp, soy hulls, cellulose) optionally vitamins (e.g., Vitamin E, C, B1, B2, B6); and minerals (e.g., calcium sources, phosphorus sources, salts, trace minerals) and various flavorants or palatants, processing aids, and preservatives to make a pet food that meets a pet's nutritional requirements and possesses the necessary aesthetic characteristics.

In one embodiment, the forage and at least one *Bacillus subtilis* strain of the invention are mixed with a concentrate. In another embodiment, the forage and at least one *Bacillus subtilis* strain of the invention are mixed with a premix or an animal feed, such as complete feed. In a further embodiment, the forage and at least one *Bacillus subtilis* strain of the invention are mixed with vitamins and/or minerals. In a further embodiment, the forage and at least one *Bacillus subtilis* strain of the invention are mixed with one or more enzymes. In a further embodiment, the forage and at least one *Bacillus subtilis* strain of the invention are mixed with other feed ingredients, such as colouring agents, stabilisers, growth improving additives and aroma compounds/flavorings, polyunsaturated fatty acids (PUFAs); reactive oxygen generating species, anti-microbial peptides, anti-fungal polypeptides and amino acids.

In a particular embodiment, the animal feed consists of or comprises milk (e.g. from sow, cow, goat, sheep), e.g. for feeding of neonatal animals. In another particular embodiment, the animal feed consists of or comprises milk replacement, e.g. for feeding of neonatal animals.

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals. Usually fat- and water-soluble vitamins, as well as trace minerals form part of a so-called premix intended for addition to the feed, whereas macro minerals are usually separately added to the feed. Non-limiting examples of fat-soluble vitamins include vitamin A, vitamin D3, vitamin E, and vitamin K, e.g. vitamin K3. Non-limiting examples of water-soluble vitamins include vitamin B12, biotin and choline, vitamin B1, vitamin B2, vitamin B6, niacin, folic acid and panthothenate, e.g. Ca-D-panthothenate. Non-limiting examples of trace minerals include boron, cobalt, chloride, chromium, copper, fluoride, iodine, iron, manganese, molybdenum, selenium and zinc. Non-limiting examples of macro minerals include calcium, magnesium, potassium and sodium.

The animal feed, animal feed additive or premix of the invention may also comprise at least one enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and beta-glucanase (EC 3.2.1.4 or EC 3.2.1.6), or any mixture thereof.

The animal feed such as the complete feed, animal feed additive or premix of the invention may further comprise one or more added amino acids. Examples of amino acids which are used in animal feed are lysine, alanine, beta-alanine, threonine, methionine and tryptophan. The animal feed, animal feed additive or premix of the invention may further comprise colouring agents, stabilisers, growth improving additives and aroma compounds/flavourings, polyunsaturated fatty acids (PUFAs); reactive oxygen generating species, anti-microbial peptides and anti-fungal polypeptides. Examples of colouring agents are carotenoids such as beta-carotene, astaxanthin and lutein. Examples of aroma compounds/flavorings are creosol, anethol, deca-, undeca- and/or dodeca-lactones, ionones, irone, gingerol, piperidine, propylidene phatalide, butylidene phatalide, capsaicin and tannin. Examples of polyunsaturated fatty acids are C18, C20 and C22 polyunsaturated fatty acids, such as arachidonic acid, docosohexaenoic acid, eicosapentaenoic acid and gamma-linoleic acid. Examples of reactive oxygen generating species are chemicals such as perborate, persulphate, or percarbonate; and enzymes such as an oxidase, an oxygenase or a syntethase.

In one embodiment, the animal feed, such as the complete feed, animal feed additive or premix comprises one or more coccidiostats.

The animal feed such as the complete feed, animal feed additive or premix further comprises a carrier. The carrier can comprise one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, whey, whey permeate, wheat flour, wheat bran, corn gluten meal, starch and cellulose.

In one embodiment, the one or more bacterial strains are stable when subjected to pressures applied/achieved during an extrusion process for pelleting. In a particular embodiment, the one or more bacterial strains are stable at pressures ranging from 1 bar to 40 bar.

In a particular embodiment, the one or more bacterial strains are stable at high temperatures. In particular, the bacterial strains are stable when they are subjected to temperatures achieved during an extrusion process for pelleting. In an even more particular embodiment, the one or more bacterial strains are stable at temperatures ranging from 70° C. to 120° C.

Animal diets can e.g. be manufactured as mash feed (non-pelleted) or pelleted feed. Typically, the milled feedstuffs are mixed and sufficient amounts of essential vitamins and minerals are added according to the specifications for the species in question. The bacteria cultures and optionally enzymes can be added as solid or liquid formulations. For example, for mash feed a solid or liquid culture formulation may be added before or during the ingredient mixing step. For pelleted feed the (liquid or solid) *Bacillus* composition may also be added before or during the feed ingredient step. Typically a liquid *Bacillus* composition of the invention comprises the bacterial strain(s) optionally with a polyol, such as glycerol, ethylene glycol or propylene glycol, and is added after the pelleting step, such as by spraying the liquid formulation onto the pellets. The bacteria may also be incorporated in an animal feed additive or premix.

The composition according to the invention may be used for the prevention, reduction or control of a bacterial colonization or infection by an obligate or opportunistic pathogen such as but not limited to Gram positive coccobacilli, cocci and rods such as *Bordetella, Staphylococcus* and *Erysipelothrix rhusiopathiae*, anaerobic sporeforming rods, such as *C. perfringens* and *C. septicum*, Lactobacillales such as Streptococcaceae, e.g. *Streptococcus canis*, Enterobacteriaceae, such as *Salmonella, E. coli, Yersinia, Klebsiella* and *Shigella, Enterobacter*, Pasteurellaceae, e.g. *Pasteurella multocida, Avibacterium, Riemerella anatipestifer, Haemophilus*, Pseudomonaceae such as *Pseudomonas aeruginosa*, as well as others such as *Brachyspira* and *Campylobacter*.

In another aspect, the invention relates to a method for the prevention, reduction or control of a bacterial colonization or infection, e.g. by *Staphylococcus* pseudintermedius and/or *Streptococcus canis*, the method comprising administering an effective amount of a strain according to the invention or a composition according to the invention to an animal in need thereof. The invention further relates to a method for the prevention, reduction or control of a bacterial colonization or infection by *E. coli* and/or *Salmonella enterica*.

Another aspect of the invention relates to a method for feeding an animal comprising administering a composition of the invention to an animal, in particular a companion animal. The invention further relates to a method for feeding a monogastric animal, e.g. a pig or poultry.

In another aspect, the invention relates to the use of at least one *Bacillus subtilis* strain of the invention or an animal feed, animal feed additive or premix comprising at least one *Bacillus subtilis* strain of the invention to improve the performance of an animal, in particular a companion animal. The invention further relates to use to improve the performance of a monogastric animal e.g. a pig or poultry.

Administration of a *Bacillus subtilis* strain of the invention may improve the health of the animal, e.g. prevent or control *Staphylococcus* pseudintermedius and/or *Streptococcus canis*, and/or *E. coli* and/or *Salmonella enterica*, and may provide improved animal performance parameters for the treated animals as compared to controls. Animal performance parameters include but are not limited to weight gain (WG), feed conversion rates (FCR), decrease of mortality and increase of European Production Efficacy Factor (EPEF).

The invention further provides a method of increasing digestibility of an animal feed, the method comprising feeding a strain according to the invention or a composition according to the invention to an animal, in particular a companion animal. The invention further provides a method of increasing digestibility of an animal feed for a monogastric animal, in particular a pig or poultry.

In another aspect, the invention relates to the use of a *Bacillus subtilis* strain of the invention or an animal feed, animal feed additive or premix comprising a *Bacillus subtilis* strain of the invention to improve the performance of an animal, in particular a monogastric animal.

Accordingly, the invention relates to use of a strain according to the invention, or a composition according to the invention, for improving one or more animal performance parameters selected from the group consisting of:
  i) increased weight gain (WG),
  ii) lower feed conversion ratio (FCR),
  iii) increase the digestibility of the feed,
  iv) lower enteritis frequency,
  v) increased European Production Efficacy Factor (EPEF), and
  vi) lower mortality.

In a preferred embodiment of the invention, "animal performance" is determined by the body weight gain of the animal and/or by the feed conversion ratio. By "improved animal performance" it is meant that there is increased body weight gain and/or reduced feed conversion ratio and/or improved digestibility of nutrients or digestible energy in a feed and/or metabolizable energy and/or increased feed efficiency resulting from the use of animal feed, animal feed additive or premix of the present invention in animal feed in comparison to animal feed which does not comprise said animal feed, animal feed additive or premix. Preferably, by "improved animal performance" it is meant that there is increased body weight gain and/or reduced feed conversion ratio.

An "increased weight gain" refers to an animal having increased body weight on being fed feed comprising a feed composition compared with an animal being fed a feed without said feed composition of the invention. Specifically, the Weight Gain of an animal is the increase of weight of the animal over a specified time period. In one embodiment, the improvement in body weight gain is of at least 0.5%, such as at least 1%, such as at least 2%, such as at least 2.5%, such as at least 3%, such as at least 4%, such as at least 5%, such as at least 6%, such as at least 7%, such as at least 8%, such as at least 9%, such as at least 10%.

In one embodiment, the improvement in weight gain results in a body weight gain of at least 0.5%, such as at least 0.8%, such as at least 1.2%, such as at least 1.5%, such as at least 1.8%, such as at least 2.0%, such as at least 2.5%, such as at least 3.0%, such as at least 4.0%, such as at least 5.0%, such as at least 6.0%, such as at least 7.0%. In a preferred embodiment, the improvement in weight gain results in a weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

In one embodiment, the improvement of feed conversion ratio (FCR) results in a FCR of −2.5% or less than −2.5%, such as less than −2.6%, such as less than −2.7%, such as less than −2.8%, such less than −2.9%, such as less than −3.0%. In a preferred embodiment, the improvement of FCR results in a FCR of from −5% to −2%, such as a FCR of from −4% to −2%, such as a FCR of from −3.5% to −2.5%. In a specific embodiment the improvement of FCR results in a FCR within an interval selected from the group consisting of from −5% to −4.5%, from −4.5% to −4%, from −4% to −3.8%, from −3.8% to −3.6%, from −3.6% to −3.4%, from −3.4% to −3.2%, from −3.2 to −3.0%, from −3.0% to −2.8% and from −2.8 to −2.5%, or any combination of these intervals.

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the feces of the subject, or between what is administered to the subject and what remains in the digesta on a specified segment of the gastrointestinal tract, e.g. the ileum. Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastrointestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, mineral digestibility and amino acid digestibility.

In another embodiment, the invention relates to a method of improving one or more animal performance parameters selected from the group consisting of
  i) increased weight gain (WG),
  ii) lower feed conversion ratio (FCR),
  iii) increase the digestibility of the feed,
  iv) lower enteritis frequency,
  v) lower necrotic enteritis mortality,
  vi) increased European Production Efficacy Factor (EPEF), and
  vii) lower mortality,
the method comprising feeding a strain according to the invention or a composition according to the invention to an animal.

A composition of the present invention may also be used for flexible feed formulation (FFF) wherein an animal is being fed with a feed having a reduced metabolizable energy and a composition of the invention whereby an acceptable animal performance and/or feed conversion ratio is obtained in spite of the reduced metabolizable energy in the feed. The reduced metabolizable energy may be in the level of from 97% to 99% of standard feed for the animal in question, such as from 97% to 98% or from 98% to 99%.

LEGEND TO FIGURES

FIG. 1

Inhibition zones of four *Bacillus subtilis* strains against *Staphylococcus* pseudintermedius KU ID30618).
  Well B2, B4, B6: DSM 32685
  Well B8, B10, B12: DSM 19489
  Well F2, F4, F6: DSM 32686
  Well F8, F10, F12: Calsporin®
Inhibition is only seen in well B2, B4 and B6 containing *Bacillus subtilis* deposited as DSM 32685.

FIG. 2

Inhibition zones of four *Bacillus subtilis* strains against *E. coli* O147:K89 F4 H19.
  Well B2, B4, B6: DSM 32685
  Well B8, B10, B12: DSM 19489
  Well E2, E4, E6: DSM 32686
  Well E8, E10, E12: Calsporin®
Inhibition is seen in well B2, B4 and B6 containing *Bacillus subtilis* deposited as DSM 32685. Inhibition is also seen in well H12 containing a positive control (the antimicrobial ciprofloxacin).

DEPOSIT AND EXPERT SOLUTION

The *Bacillus subtilis* strain DSM 19489 has been deposited at DSMZ (Deutsche Sammlung von Mikroorganismen und Zellkulturen GmbH, Inhoffenstrasse 7B, D-38124 Braunschweig) on Jun. 27, 2007 by Chr. Hansen A/S, Denmark. The deposit has been made under the conditions of the Budapest Treaty on the International Recognition of the Deposit of Microorganisms for the Purposes of Patent Procedure.

The *Bacillus subtilis* strain DSM 32685 has been deposited at DSMZ (Deutsche Sammlung von Mikroorganismen und Zellkulturen GmbH, Inhoffenstrasse 7B, D-38124 Braunschweig) on Nov. 15, 2017 by Chr. Hansen A/S, Denmark. The deposit has been made under the conditions of the Budapest Treaty on the International Recognition of the Deposit of Microorganisms for the Purposes of Patent Procedure.

The *Bacillus subtilis* strain DSM 32686 has been deposited at DSMZ (Deutsche Sammlung von Mikroorganismen und Zellkulturen GmbH, Inhoffenstrasse 7B, D-38124 Braunschweig) on Nov. 15, 2017 by Chr. Hansen A/S, Denmark. The deposit has been made under the conditions of the Budapest Treaty on the International Recognition of the Deposit of Microorganisms for the Purposes of Patent Procedure.

For all of the above-identified deposited microorganisms, the following additional indications apply:

As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn.

EXAMPLES

Example 1

Pathogen Inhibition
Materials
Veal Infusion Broth (VIB) (BD, Franklin lakes, NJ USA; Difco catalogue number 234420) Brain heart infusion broth (BHI) (Thermo Fischer, Waltham, MA, USA; Oxoid catalogue number CM1135)
Luria-bertani agar (LB) (Per liter: 10 g peptone, 5 g yeast extract, 5 g sodium chloride) Maximum recovery diluent (MRD) (Thermo Fischer, Waltham, MA, USA; Oxoid catalogue number TV5016D)
Tryptone soya agar+5% Sheep blood (TSA+SB) (Thermo Fischer, Waltham, MA, USA; Oxoid catalogue number PB5012A)
Omni tray/single well plates N 242811) (Thermo Fischer, Waltham, MA, USA)/NUNC Denmark
Immuno TSP sterile plates (VWR, Radnor, PA, USA) catalogue number 735-0022 Syringe filters 0.2 µm
Pathogen Strains:
*Streptococcus canis* DTU837 (Technical University of Denmark)
*Staphylococcus* pseudintermedius DTU4438 (Technical University of Denmark)
*Staphylococcus* pseudintermedius KU ID30243 (University of Copenhagen, Denmark)
*Staphylococcus* pseudintermedius KU ID30618 (University of Copenhagen, Denmark)
*Staphylococcus* pseudintermedius KU ID30377 (University of Copenhagen, Denmark)
The pathogen strains were maintained in BHI with 20% glycerol at −80° C.

Bacillus subtilis Strains:

The *Bacillus subtilis* strain DSM 32685 was isolated from feces from a dog born and raised in Denmark and the *Bacillus subtilis* strain DSM 32686 was isolated from feces from a cat born and raised in Denmark. DSM 19489 and a *Bacillus subtilis* strain isolated from the product Calsporin® brought on the market by Asahi Calpis Co., Ltd. Japan, in the following termed "Calsporin®" were used as reference strains.

The *Bacillus subtilis* strains were maintained in VIB with 20% glycerol at −80° C.

DSM 32685 and DSM 32686 were screened for antibiotic susceptibility according to "Guidance on the assessment of bacterial susceptibility to inhibitorys of human and veterinary importance." EFSA Journal 2012; 10(6):2740 and found to be susceptible to all antibiotics and that growth was below the EFSA cut-off values in all cases. Screening for biogenic amine production and cytotoxicity was also done with negative results.

Screening for Inhibition of *Staphylococcus* Pseudintermedius

The four *Staphylococcus* pseudintermedius strains were suspended in MRD until McFarland 0.5 was obtained and 60 µL of the pathogen suspension was diluted in approximately 100 ml melted LB agar (max. 42° C.). The inoculated agar was poured into Omni Tray Single-well plates, Immuno TSP plates were attached. After drying the immune TSP plates were removed and the wells were inoculated with 5 µL overnight culture (triplicates) of *Bacillus* test strains. The plates were incubated aerobically at 30° C., n=2 for 48 hours.

For each of the pathogens two replicate plates were used with the following positioning of the *Bacillus subtilis* strains:

Well B2, B4, B6: DSM 32685

Well B8, B10, B12: DSM 19489

Well F2, F4, F6: DSM 32686

Well F8, F10, F12: Calsporin®

The concentration of *Staphylococcus* pseudintermedius was determined to be $1 \times 10^8$ CFU/ml, based on the McFarland 0.5 suspension by serial dilution and plating on TSA+SB agar with 24 hour incubation at 37° C. The concentration of *Staphylococcus* pseudintermedius in the inoculated agar was therefore estimated to be $1 \times 10^8$ CFU/ml/(100 ml/0.06 ml)=$6 \times 10^4$ CFU/ml.

Screening for Inhibition of *Streptococcus canis*

BHI broth (20 ml) was inoculated with *Streptococcus canis* (aiming for $5 \times 10^1$ CFU/ml broth) and test samples were added (2 ml sterile filtered culture). The samples were incubated at 37° C. under aerobic conditions for up to 48 hours. Samples for CFU counts were collected at $T_0$ (immediately after the pathogen and test sample was added) and after 24 h and 48 h of incubation, (n=3). TSA+SB agar plates were used for enumeration of *Streptococcus canis*. Plates were incubated aerobically at 37° C. for 1-2 days.

Results

TABLE 1

Inhibition of *Staphylococcus pseudintermedius* by *Bacillus subtilis* strains (n = 6)

| | | Staphylococcsus pseudintermedius (radii of clearing zone) (mm) | | | |
|---|---|---|---|---|---|
| Strain | DSM # | DTU4438 | KU ID30243 | KU ID30618 | KU ID30377 |
| B. subtilis | 32685 | 3 | 3 | 3 | 3 |
| B. subtilis | 19489 | 0 | 0 | 0 | 0 |
| B. subtilis | 32686 | 0 | 0 | 0 | 0 |
| B. subtilis | Calsporin ® | 0 | 0 | 0 | 0 |

Figure 1:
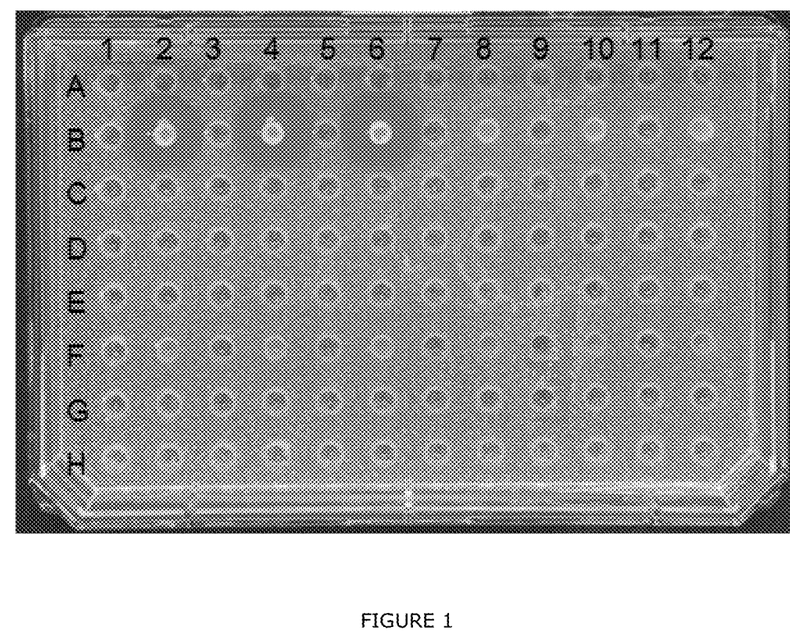

The results in Table 1 show that *Bacillus subtilis* DSM 32685 inhibited the growth of *Staphylococcus* pseudintermedius. No inhibition was observed with the three other *Bacillus subtilis* strains tested. A representative example of the inhibition zones is shown in FIG. 1 and shows a clear difference between inhibition and no inhibition.

TABLE 2

Inhibition of *Streptococcus canis* DTU837

| | Log10 CFU ($T_0$) | Log10 CFU ($T_{24}$) | Log10 growth ($T_{24} - T_0$) |
|---|---|---|---|
| DSM 32685 | 1.8 | 5.1 | 3.3 |
| DSM 32686 | 1.8 | 8.5 | 6.7 |
| DSM 19489 | 1.7 | 9.2 | 7.5 |
| Calsporin ® | 1.8 | 8.6 | 6.8 |
| Control tube | 1.7 | 8.4 | 6.7 |

The results in table 2 show that *Bacillus subtilis* strains DSM 19489 and Calsporin® had comparable or higher number of *Streptococcus canis* DTU837 than the control tube after 24 hours of incubation. In the presence of *Bacillus subtilis* strain DSM 32685 supernatant *Streptococcus canis* DTU837 grew 1000 fold less than the control tube, clearly demonstrating an inhibitory effect.

Example 2

Measurement of Amount of Reducing Sugars in Feed Incubated with a *Bacillus* Composition The objective of this experiment was to examine the ability of different *Bacillus subtilis* strains to degrade NSP in commercial dog feed and increase the available sugar amount.

Materials

Sodium phosphate buffer 100 mM pH=6.7 (Merck, Darmstadt, Germany; catalogue number: 1.06586)

Pierce® BCA protein Assay Kit (Thermo Fischer, Waltham, MA, USA, catalogue number: PIE-23225)

Dog feed (Carrier Chicken and Rice) composition: Chicken 26%, rice 20%, maize, barley, fat of animal and vegetable origin, linseed, beet fibre, dryed egg components, yeast, fructo-oligosaccarides (FOS), glucoseamine, rosemary and minerals (Svenska Hundfoder, Stenstorp, Sweden)

Method

The dog feed was autoclaved at 121° C. for 15 min for sterilization. Then triplicate feed samples were diluted 20 fold with sodium phosphate buffer to ensure a pH at about 6-6.5 throughout the whole experiment. *Bacillus subtilis* inoculation was done by adding 2% overnight culture of the *Bacillus subtilis* strains, grown in VIB. A sample was taken for analysis for reducing sugar (DNS) (T=0). After incubation at 37° C. for 24 hours the samples were centrifuged and the supernatant used for determining DNS.

Reducing sugar was analyzed by 3.5-dinitrosalicylic acid (DNS) assay as follows: Na-acetate buffer (100 mM, pH 6) was mixed with sterile filtered *Bacillus subtilis* supernatant and incubated at 40° C. for 10 min. DNS reagent was added to the test tube, mixed and incubated in a boiling water bath for 5 min. After cooling, absorbance was measured at 540 nm in a spectrophotometer.

A standard curve was established with a glucose stock solution for presenting results in reducing sugar or enzyme units (amount of enzyme needed to release 1 µmol reducing glucose equivalent in 1 ml per time unit).

The experiment was repeated twice and results are reported as an average.

Results

TABLE 3

Reducing sugar increase over control in presence of three *Bacillus subtilis* strains (n = 2)

|  | ΔKj/Kg feed | Standard deviation |
|---|---|---|
| Dog feed + DSM 32685 | 685 | 27 |
| Dog feed + DSM 19489 | 438 | 37 |
| Dog feed + Calsporin ® | 117 | 9 |

The results in table 3 show that *Bacillus subtilis* DSM 32685 was superior to the 2 other strains tested in releasing sugar from dog feed based on the DNS method.

Example 3

Pathogen Inhibition
Pathogen Strains:
*Escherichia coli* O147:K89 F4 H19 (Statens Serum Institute, Copenhagen, Denmark)
*Escherichia coli* O149:k91, k88a, c:h10 NCTC10650 (National Collection of Type Cultures, England)
*Salmonella enterica* serovar Heidelberg, found in DK 2011, from imported chicken meat from Brazil (Technical University of Denmark, Kgs. Lyngby)
*Salmonella enterica* serovar *Infantis* (S. inf. 1; SGSC2483 received from St. Hycinth, Canada; Salmonella Genetic Stock Centre, Department of Biological Sciences 2500 University Dr. N.W., Calgary, Alberta, Canada)
*Salmonella enterica* serovar Enteritidis (IMASDE, Madrid, Spain)
*Salmonella enterica* serovar Schwarzengrund (S. sch. 1; received from St. Hycinth, Canada; Salmonella Genetic Stock Centre, Department of Biological Sciences 2500 University Dr. N.W., Calgary, Alberta, Canada)
*Salmonella enterica* serovar Typhimurium (I 4,5,12:i:1, 2), ATCC14028

The pathogen strains were maintained in BHI with 20% glycerol at −80° C.

Screening for Inhibition of *E. coli* and *Salmonella* Spp.:

The seven pathogenic *E. coli* and *Salmonella* spp. strains were each suspended in MRD until McFarland 0.5 was obtained and 10 µL of each pathogen suspension was diluted in approximately 35 ml melted LB agar (max. 42° C.). The inoculated agar was poured into Omni Tray Single-well plates, Immuno TSP plates were attached. After drying the immune TSP plates were removed and the wells were inoculated with 5 µL overnight culture (triplicates) of *Bacillus* test strains. The plates were incubated aerobically at 30° C. for 48 hours. For the *E. coli* plates, two replicate plates were used (n=2); for the 10 *Salmonella* spp. plates, one replicate plate was used (n=1).

The following positioning of the *Bacillus subtilis* strains on the plates containing the pathogens was used:
Well B2, B4, B6: DSM 32685
Well B8, B10, B12: DSM 19489
Well E2, E4, E6: DSM 32686
Well E8, E10, E12: Calsporin®

The concentration of *E. coli* and *Salmonella* spp. in the inoculated agar was estimated to be $2.9 \times 10^4$ CFU/ml.

Results

TABLE 4

Inhibition of *E. coli* O147, *E. coli* O149, Salmonella Heidelberg, S. Infantis, S. Enteritidis, S. Schwarzengrund, & S. Typhimurium by *Bacillus subtilis* strains.

| | | Radii of clearing zone (mm) | | | | | | |
|---|---|---|---|---|---|---|---|---|
| Strain | DSM # | E. coli O147 | E. coli O149 | S. Heidelberg | S. Infantis | S. Enteritidis | S. Schwarzengrund | S. Typhimurium |
| B. subtilis | 32685 | 2 | 2 | 2 | 2 | 2 | 2 | 2 |
| B. subtilis | 19489 | 0 | 0 | 0 | 0 | 0 | 0 | 0 |
| B. subtilis | 32686 | 0 | 0 | 0 | 0 | 0 | 0 | 0 |
| B. subtilis | Calsporin® | 0 | 0 | 0 | 0 | 0 | 0 | 0 |

Figure 2:
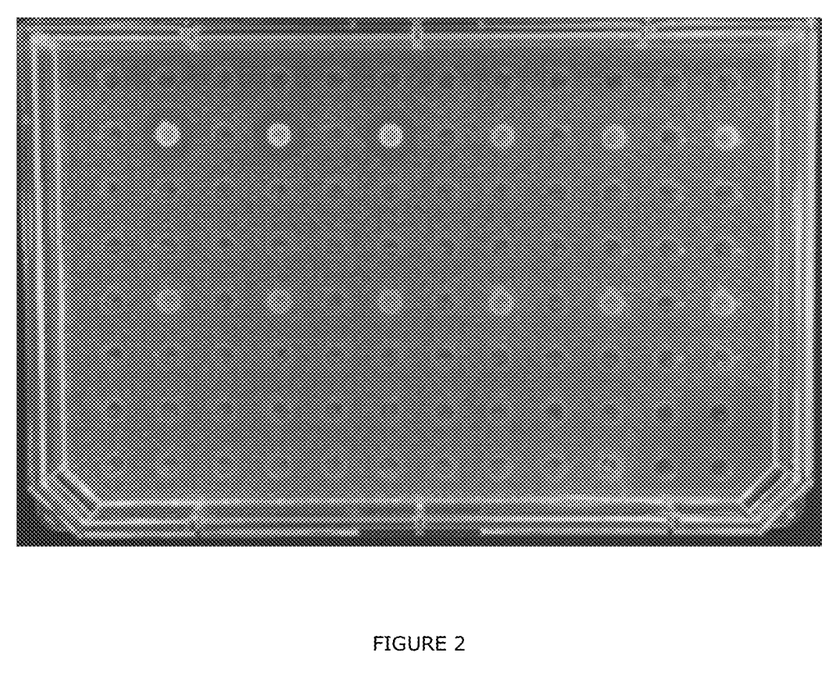

The results in Table 4 show that *Bacillus subtilis* DSM 32685 inhibited the growth of *E. coli* O147, *E. coli* O149, *Salmonella* Heidelberg, S. infantis, S. Enteritidis, S. Schwarzengrund, & S. Typhimurium. No inhibition was observed with the three other *Bacillus subtilis* strains tested. A representative example of the inhibition zones is shown in FIG. 2 and shows a clear difference between inhibition and no inhibition.

The invention claimed is:

1. A method for inhibiting a bacterial colonization or bacterial infection by one or more of *Staphylococcus* pseudintermedius, *Staphylococcus carnosus*, *Salmonella enterica*, *Salmonella* Newport, *Streptococcus canis*, *Escherichia coli*, and *Clostridium perfringens*, the method comprising administering to an animal in need thereof an effective amount of a *Bacillus subtilis* strain deposited at Deutsche Sammlung von Mikroorganismen und Zellkulturen GmbH, Braunschweig, Germany (DSMZ) under accession number DSM 32685, wherein strain DSM 32685:

(i) exhibits susceptibility to ampicillin, vancomycin, gentamicin, kanamycin, streptomycin, erythromycin, clindamycin, tetracycline, and chloramphenicol when tested under CLSI guidelines M07-A8 and M45-A2;
(ii) exhibits an inhibition zone of at least 1 mm for *Staphylococcus* pseudintermedius, *Escherichia coli*, and *Salmonella enterica;*
(iii) reduces the growth rate of *Streptococcus canis* by at least one $\log_{10}$ growth in 24 hours; and
(iv) inhibits growth of *Staphylococcus carnosus, Salmonella* Newport, and *Clostridium perfringens*.

2. The method according to claim 1, wherein the method is effective for improving one or more animal performance parameters selected from the group consisting of
i) increased weight gain (WG),
ii) lower feed conversion ratio (FCR),
iii) increased digestibility of the feed,
iv) lower enteritis frequency,
v) increased European Production Efficacy Factor (EPEF), and
vi) lower mortality.

3. The method according to claim 1, wherein the administered *Bacillus subtilis* strain is in the form of spores.

4. The method according to claim 1, wherein the *Bacillus subtilis* strain is administered in a composition that further comprises one or more bacteria of one or more genera selected from *Lactobacillus, Lactococcus, Streptococcus, Bacillus, Pediococcus, Enterococcus, Leuconostoc, Carnobacterium, Propionibacterium, Bifidobacterium, Clostridium*, and *Megasphaera*.

5. The method according to claim 1, wherein the *Bacillus subtilis* strain is administered in a composition that further comprises one or more types of yeast.

6. The method according to claim 1, wherein the *Bacillus subtilis* strain is administered in a format selected from a direct fed microbial, an animal feed premix, an animal feed additive, and a complete animal feed.

7. A method for feeding an animal, comprising administering to an animal a *Bacillus subtilis* strain deposited at DSMZ under accession number DSM 32685, wherein strain DSM 32685:
(i) exhibits susceptibility to ampicillin, vancomycin, gentamicin, kanamycin, streptomycin, erythromycin, clindamycin, tetracycline, and chloramphenicol when tested under CLSI guidelines M07-A8 and M45-A2;
(ii) exhibits an inhibition zone at least 1 mm for *Staphylococcus* pseudintermedius, *Escherichia coli*, and *Salmonella enterica;*
(iii) reduces the growth rate of *Streptococcus canis* by at least one $\log_{10}$ growth in 24 hours; and
(iv) inhibits growth of *Staphylococcus carnosus, Salmonella* Newport, and *Clostridium perfringens*.

8. The method according to claim 7, wherein the animal is a monogastric animal.

9. The method according to claim 7, wherein the administered *Bacillus subtilis* strain is in the form of spores.

10. The method according to claim 7, wherein the *Bacillus subtilis* strain is administered in a composition that further comprises one or more bacteria of one or more genera selected from *Lactobacillus, Lactococcus, Streptococcus, Bacillus, Pediococcus, Enterococcus, Leuconostoc, Carnobacterium, Propionibacterium, Bifidobacterium, Clostridium*, and *Megasphaera*.

11. The method according to claim 7, wherein the *Bacillus subtilis* strain is administered in a composition that further comprises one or more types of yeast.

12. The method according to claim 7, wherein the *Bacillus subtilis* strain is administered in an animal feed composition.

* * * * *